(12) United States Patent
Kamohara et al.

(10) Patent No.: US 7,875,695 B2
(45) Date of Patent: Jan. 25, 2011

(54) HYDROPHILIC ORGANOPOLYSILOXANE COMPOSITION FOR USE AS DENTAL IMPRESSION MATERIAL

(75) Inventors: Hiroshi Kamohara, Tokyo (JP); Toshiyuki Ozai, Annaka (JP); Hideki Sugahara, Annaka (JP)

(73) Assignees: GC Corporation, Tokyo (JP); Shin-Etsu Chemical Co., Ltd., Tokyo (JP)

(*) Notice: Subject to any disclaimer, the term of this patent is extended or adjusted under 35 U.S.C. 154(b) by 108 days.

(21) Appl. No.: 12/251,252

(22) Filed: Oct. 14, 2008

(65) Prior Publication Data

US 2010/0069525 A1 Mar. 18, 2010

(30) Foreign Application Priority Data

Sep. 18, 2008 (JP) ............... 2008-239551

(51) Int. Cl.
*C08G 77/20* (2006.01)
(52) U.S. Cl. ............... 528/32; 528/10; 528/25; 528/30; 528/31; 528/33; 523/109; 525/478
(58) Field of Classification Search ......... 523/109; 525/478; 528/10, 30, 31, 32, 33, 25
See application file for complete search history.

(56) References Cited

U.S. PATENT DOCUMENTS 4,877,854 A 10/1989 Hattori et al.
5,403,885 A 4/1995 Voigt et al.
5,849,812 A * 12/1998 Zech et al. ............... 523/109
5,907,002 A 5/1999 Kamohara et al.
6,861,457 B2 3/2005 Kamohara
7,456,246 B2 11/2008 Kamohara et al.

FOREIGN PATENT DOCUMENTS

| JP | 6-37558 B2 | 5/1989 |
| JP | 2003-81732 A | 3/2003 |
| JP | 2004-182823 A | 7/2004 |
| WO | WO 99/62461 A1 | 12/1999 |

OTHER PUBLICATIONS

EP 08 25 3334, European Search Report, Sep. 7, 2010, 6 pages.

* cited by examiner

*Primary Examiner*—Kuo-Liang Peng
(74) *Attorney, Agent, or Firm*—Birch, Stewart, Kolasch & Birch, LLP

(57) ABSTRACT

A hydrophilic organopolysiloxane composition of the hydrosilylation reaction cure type for use as dental impression material is characterized by comprising as essential components (A) a diorganopolysiloxane having at least 0.1 silicon-bonded alkenyl group in a molecule, (B) a liquid or solid organopolysiloxane having average compositional formula (1), comprising $SiO_2$ units and $R_3SiO_{1/2}$ units (R is a monovalent hydrocarbon, alkoxy or hydroxyl group) and having a viscosity of at least 10 mPa·s at 23° C., (C) an organohydrogenpolysiloxane having at least two silicon-bonded hydrogen atoms in a molecule, (D) a hydrosilylation catalyst, and (E) a polyether having average compositional formula (2).

11 Claims, No Drawings

HYDROPHILIC ORGANOPOLYSILOXANE COMPOSITION FOR USE AS DENTAL IMPRESSION MATERIAL

BACKGROUND OF THE INVENTION

This invention relates to a hydrophilic organopolysiloxane composition for use as dental impression material which cures into a hydrophilic elastomeric or gel-like product (cured silicone rubber or cured silicone gel).

At the present, organopolysiloxane compositions are commonly used in main applications including building, electric/electronic, and dental fields. This material, however, has several problems due to the nature of siloxane that it is water repellent in itself. For example, in the building field, the surface of the material is not receptive to aqueous paints. When used as an impression material in the dental field, the material is difficult to produce precise impressions.

Approaches to these problems include the use of hydrophilic fillers such as calcium carbonate in the building field and the addition of polyether in the dental field (JP-A 2003-81732). Such approaches are insufficient in these fields since the base is dimethylpolysiloxane. The addition of only the filler leads to variant coating of aqueous paint. The internal addition of polyether allows for impression variations because the polyether can separate out of the composition or cured product thereof with the lapse of time.

JP-B 6-37558 discloses a curable composition comprising an allyl-terminated polyether as a base and a polyether-modified organohydrogenpolysiloxane as a crosslinking agent. This composition has the problems that the crosslinking agent is difficult to synthesize and the composition loses a curing ability with the lapse of time because of internal rearrangement of allyl groups at the ends of the base under the oxidizing action of a platinum catalyst.

SUMMARY OF THE INVENTION

An object of the invention is to provide a hydrophilic organopolysiloxane composition which is curable and stable in that the cured product thereof is fully hydrophilic and prevents polyether from separating out over time, and which composition also has a high strength in the cured state and enables to take an accurate impression so that the composition is best suited for use as a dental impression material.

Making extensive investigations to achieve the above and other objects, the inventors developed a composition comprising a base polymer containing at least 5 mol % of diphenylsiloxane units which composition prevents separation of polyether from the siloxane and minimizes variation of coating of aqueous paint or variations of impressions, as disclosed in JP-A 2004-182823. Some compositions, however, are weak in material strength in taking impressions, failing to take accurate impressions.

Continuing further investigations, the inventors have found that by using as a base polymer a curable diorganopolysiloxane having at least 0.1 silicon-bonded alkenyl group in a molecule, especially a curable diorganopolysiloxane containing at least 5 mol % of diphenylsiloxane units or at least 10 mol % of methylphenylsiloxane units and having at least 0.1 silicon-bonded alkenyl group in a molecule, or using as a base polymer a curable diorganopolysiloxane having at least 0.1 silicon-bonded alkenyl group in a molecule, preferably in combination with a diorganopolysiloxane containing at least 3 mol % of diphenylsiloxane units or at least 6 mol % of methylphenylsiloxane units, and free of silicon-bonded alkenyl groups in a molecule, further blending the base polymer with a liquid or solid organopolysiloxane of specific structure containing $SiO_2$ units and having a viscosity of at least 10 mPa·s at 23° C., and combining the base polymer with a polyether containing alkenyl groups in a molecule, a hydrophilic organopolysiloxane composition is obtained which cures into a fully hydrophilic product having improved tear strength. The composition or the cured product thereof inhibits separation of the polyether even after a long term of storage. From the composition, impressions with minimized variation can be taken.

Accordingly, the invention provides a hydrophilic organopolysiloxane composition for use as dental impression material as defined below.

[1] A hydrophilic organopolysiloxane composition of the hydrosilylation reaction cure type for use as dental impression material, comprising as essential components, (A) a diorganopolysiloxane having at least 0.1 silicon-bonded alkenyl group in a molecule, (B) a liquid or solid organopolysiloxane having the average compositional formula (1):

$$R_pSiO_{(4-p)/2} \quad (1)$$

wherein R is each independently a substituted or unsubstituted monovalent hydrocarbon group, alkoxy or hydroxyl group, 0.1 to 80 mol % of the entire R being alkenyl, and p is a positive number satisfying $1 \leq p < 2$, said organopolysiloxane comprising $SiO_2$ units and $R_3SiO_{1/2}$ units and having a viscosity of at least 10 mPa·s at 23° C., (C) an organohydrogenpolysiloxane having at least two silicon-bonded hydrogen atoms in a molecule, (D) a hydrosilylation catalyst, and (E) a polyether having the average compositional formula (2):

$$R^1O(C_2H_4O)_m(C_3H_6O)_nR^1 \quad (2)$$

wherein $R^1$ is a group $C_3H_6SiR^2_k(OR^2)_{3-k}$ or a monovalent hydrocarbon group, $R^2$ is a monovalent hydrocarbon group, k is 0, 1, 2 or 3, a plurality of $R^1$ and a plurality of $R^2$ may be the same or different, at least two of $R^1$ and $R^2$ are alkenyl, m is an integer of 0 to 100, n is an integer of 0 to 350, and m+n is an integer of 3 to 350.

[2] The hydrophilic organopolysiloxane composition for use as dental impression material of [1], further comprising as an essential component (F) a diorganopolysiloxane containing at least 3 mol % of diphenylsiloxane units or at least 6 mol % of methylphenylsiloxane units, and free of silicon-bonded alkenyl groups in a molecule.

[3] The hydrophilic organopolysiloxane composition for use as dental impression material of [1] or [2] wherein component (E) is present in an amount of 10 to 100 parts by weight per 100 parts by weight of components (A), (B), and (C) combined.

The hydrophilic organopolysiloxane composition of the invention cures into an elastomeric or gel-like silicone product having high hydrophilicity, improved tear strength, and minimized impression variations, and capable of inhibiting separation of polyether over time. The composition is thus best suited for use as a dental impression material.

DETAILED DESCRIPTION OF THE INVENTION

Component (A) is a curable diorganopolysiloxane serving as a base polymer in the inventive composition. The curable diorganopolysiloxane should have at least 0.1 silicon-bonded alkenyl group in a molecule. It preferably contains at least 5 mol % (typically 5 to 50 mol %), more preferably 5 to 40 mol %, and even more preferably 10 to 30 mol % of diphenylsiloxane units in the diorganosiloxane units of which the main chain is composed, or preferably contains at least 10 mol % (typically 10 to 50 mol %), more preferably 20 to 40 mol %, and even more preferably 25 to 35 mol % of methylphenylsiloxane units in the diorganosiloxane units of which the main chain is composed. If the content of diphenylsiloxane or methylphenylsiloxane units is below the range, it is desirably used in combination with (F) a nonfunctional diorganopolysiloxane, specifically diorganopolysiloxane containing at least 3 mol % of diphenylsiloxane units or at least 6 mol % of methylphenylsiloxane units, and free of silicon-bonded alkenyl groups in a molecule, to be described later. Note that the term "nonfunctional" means that the diorganopolysiloxane does not participate in hydrosilylation addition reaction.

While the curable diorganopolysiloxane (A) has on the average at least 0.1 silicon-bonded alkenyl group in a molecule, the preferred organopolysiloxane has on the average at least 0.5, more preferably at least 0.8, and even more preferably at least 2 silicon-bonded alkenyl groups.

Most often, the alkenyl-containing organopolysiloxane has the average compositional formula (i):

$$R^3_a SiO_{(4-a)/2} \quad (i)$$

wherein $R^3$ is each independently a substituted or unsubstituted monovalent hydrocarbon group of 1 to 10 carbon atoms, and preferably 1 to 8 carbon atoms, and "a" is a positive number of 1.95 to 2.05, and preferably 2.00 to 2.02.

Examples of the silicon-bonded, substituted or unsubstituted, monovalent hydrocarbon groups represented by $R^3$ include alkyl groups such as methyl, ethyl, propyl, isopropyl, butyl, isobutyl, tert-butyl, pentyl, neopentyl, hexyl, cyclohexyl, octyl, nonyl and decyl; aryl groups such as phenyl, tolyl, xylyl, and naphthyl; aralkyl groups such as benzyl, phenylethyl, and phenylpropyl; alkenyl groups such as vinyl, allyl, propenyl, isopropenyl, butenyl, hexenyl, cyclohexenyl and octenyl; and substituted forms of the foregoing groups in which some or all hydrogen atoms are replaced by halogen atoms (e.g., fluoro, bromo, chloro), cyano groups or the like, for example, halo-substituted alkyl groups such as chloromethyl, chloropropyl, bromoethyl and trifluoropropyl, and cyanoethyl.

On the average, at least 0.1, preferably at least 0.5, more preferably at least 0.8, and even more preferably at least 2 of $R^3$ are alkenyl groups, preferably of 2 to 8 carbon atoms, and more preferably 2 to 6 carbon atoms. The content of alkenyl is preferably 0.0001 to 20 mol %, more preferably 0.001 to 10 mol %, and even more preferably 0.01 to 5 mol %, based on the entire organic groups $R^3$ (i.e., substituted or unsubstituted monovalent hydrocarbon groups). The alkenyl group may be attached to a silicon atom at the end or a silicon atom at an intermediate position of the molecular chain or both. The inclusion of at least alkenyl groups attached to silicon atoms at both ends of the molecular chain is preferred. Groups $R^3$ other than alkenyl are preferably methyl or phenyl.

The organopolysiloxane should preferably have a viscosity at 23° C. of 10 to 500,000 mPa·s, more preferably 40 to 200,000 mPa·s. A viscosity of less than 10 mPa·s at 23° C. invites a tendency that the resulting silicone rubber has substantially degraded physical properties. A viscosity in excess of 500,000 mPa·s invites a tendency that the resulting silicone rubber is inefficient to handle or work. It is noted that the viscosity as used herein is measured by a rotational viscometer or the like.

With respect to the molecular structure, the organopolysiloxane is a diorganopolysiloxane having a main chain consisting essentially of repeating diorganosiloxame units and capped with triorganosiloxy groups at both ends of the molecular chain. The main chain may partially contain a minor amount of trifunctional siloxane units.

Also, the organopolysiloxane may be a homopolymer having such a molecular structure, a copolymer having such a molecular structure, or a mixture of these polymers. Desirably the organopolysiloxane contains at least 5 mol % of diphenylsiloxane units or at least 10 mol % of methylphenylsiloxane units in the diorganosiloxane units of the main chain, when taken as the overall base polymer. Then, for example, a mixture of 50 parts by weight of a dimethylpolysiloxane capped with dimethylvinylsiloxy at both ends of the molecular chain and containing 10 mol % of diphenylsiloxane and 50 parts by weight of a dimethylpolysiloxane capped with dimethylvinylsiloxy at both ends of the molecular chain may be used.

Examples of the organopolysiloxane which can serve as the base polymer include dimethylpolysiloxane capped with dimethylvinylsiloxy at both ends of the molecular chain, dimethylpolysiloxane capped with methyldivinylsiloxy at both ends of the molecular chain, dimethylsiloxane (80 mol %)-methylphenylsiloxane (20 mol %) copolymers capped with dimethylvinylsiloxy at both ends of the molecular chain, dimethylsiloxane (80 mol %)-diphenylsiloxane (20 mol %) copolymers capped with dimethylvinylsiloxy at both ends of the molecular chain, dimethylsiloxane (90 mol %)-diphenylsiloxane (10 mol %) copolymers capped with dimethylvinylsiloxy at both ends of the molecular chain, and dimethylsiloxane-methylvinylsiloxane copolymers capped with trimethylsiloxy at both ends of the molecular chain.

Component (B) is a liquid or solid organopolysiloxane resinous copolymer of branched or three-dimensional network structure having the average compositional formula (1):

$$R_p SiO_{(4-p)/2} \quad (1)$$

wherein R is each independently a substituted or unsubstituted monovalent hydrocarbon group, alkoxy or hydroxyl group, 0.1 to 80 mol % of the entire R being alkenyl, and p is a positive number satisfying $0 \leq p < 2$, preferably $0.5 \leq p \leq 1.8$, and more preferably $0.7 \leq p \leq 1.5$, the organopolysiloxane comprising $SiO_2$ units and $R_3SiO_{1/2}$ units and having a viscosity of at least 10 mPa·s at 23° C.

In formula (1), R stands for substituted or unsubstituted monovalent hydrocarbon groups attached to silicon atoms, typically those of 1 to 12 carbon atoms, preferably 1 to 8 carbon atoms. Examples include alkyl groups such as methyl, ethyl, propyl, isopropyl, butyl, isobutyl, tert-butyl, pentyl, neopentyl, hexyl, cyclohexyl, octyl, nonyl and decyl; aryl groups such as phenyl, tolyl, xylyl, and naphthyl; aralkyl groups such as benzyl, phenylethyl, and phenylpropyl; alkenyl groups such as vinyl, allyl, propenyl, isopropenyl, butenyl, hexenyl, cyclohexenyl and octenyl; and substituted forms of the foregoing groups in which some or all hydrogen atoms are replaced by halogen atoms (e.g., fluoro, bromo, chloro), cyano groups or the like, for example, halo-substituted alkyl groups such as chloromethyl, chloropropyl, bromoethyl and trifluoropropyl, and cyanoethyl.

It is preferred that at least two of R be alkenyl, preferably having 2 to 8 carbon atoms, and more preferably 2 to 6 carbon atoms. Differently stated, the content of alkenyl is about 0.1 to 80 mol %, preferably about 0.5 to 50 mol %, and more preferably about 1 to 30 mol % of the entire organic groups R (i.e., substituted or unsubstituted monovalent hydrocarbon groups).

The organopolysiloxane as component (B) is a resinous copolymer comprising $SiO_2$ units and $R_3SiO_{1/2}$ units. It may consist of $SiO_2$ units and $R_3SiO_{1/2}$ units or if desired, additionally contain $R_2SiO_{2/2}$ units and/or $RSiO_{3/2}$ units (wherein R is as defined above) in a total amount of up to 50% (i.e., 50% to 0%), preferably up to 40% (i.e., 40% to 0%), and more preferably up to 30% (i.e., 30% to 0%), based on the total weight of the organopolysiloxane resinous copolymer. The molar ratio of $R_3SiO_{1/2}$ units to $SiO_2$ units, $[R_3SiO_{1/2}/SiO_2]$ should desirably be from 0.5:1 to 1.5:1, more desirably from 0.7:1 to 1.3:1. If this molar ratio is less than 0.5 or more than 1.5, the effect of enhancing the mechanical strength of the cured product may not be fully exerted, or the separation with time of polyether from the composition or cured product thereof may not be inhibited, depending on the type of component (A) as the base polymer. The resinous copolymer as component (B) should desirably contain $5 \times 10^{-3}$ to $1 \times 10^{-4}$ mol/g, and more desirably $3 \times 10^{-3}$ to $2 \times 10^{-4}$ mol/g of alkenyl groups (typically vinyl). An alkenyl content of more than $5 \times 10^{-3}$ mol/g may result in a cured product becoming hard and brittle whereas an alkenyl content of less than $1 \times 10^{-4}$ mol/g may fail to achieve the mechanical strength enhancement effect.

The organopolysiloxane as component (B) should have a viscosity at 23° C. of at least 10 mPa-s, preferably at least 100 mPa-s, and more preferably at least 1,000 mPa-s. If the viscosity is below the range, the cured product may have poor mechanical strength. No upper limit is imposed on the viscosity of component (B), that is, it may be solid at 23° C.

The amount of organopolysiloxane (B) blended is preferably 5 to 50 parts, more preferably 5 to 40 parts, and even more preferably 10 to 30 parts by weight per 100 parts by weight of component (A). If the amount of component (B) blended is below the range, the cured product may have poor mechanical strength, and the composition or cured product thereof may allow the polyether to separate out with the lapse of time, depending on the type of component (A) as the base polymer. If the amount of component (B) is excessive, the cured product may be less hydrophilic.

Component (C) is a curing or crosslinking agent for curing the organopolysiloxanes as components (A) and (B). It is an organohydrogenpolysiloxane containing on the average at least two silicon-bonded hydrogen atoms (i.e., SiH groups) in a molecule.

The organohydrogenpolysiloxane serves as a crosslinking agent for curing the composition through hydrosilylation addition reaction with the alkenyl-containing organopolysiloxanes as components (A) and (B). Most often, it is represented by the following average compositional formula (ii):

$$R^4_b H_c SiO_{(4-b-c)/2} \quad (ii)$$

wherein $R^4$ is a substituted or unsubstituted monovalent hydrocarbon group having 1 to 10 carbon atoms, "b" is a positive number of 0.7 to 2.1, "c" is a positive number of 0.001 to 1.0, and b+c is from 0.8 to 3.0. Preferred are those of formula (ii) having at least two (typically 2 to about 300), more preferably at least three (typically 3 to about 200), most preferably 4 to 100 silicon-bonded hydrogen atoms (SiH groups) in a molecule.

Examples of the monovalent hydrocarbon group represented by $R^4$ are as exemplified above for $R^3$ in formula (i) although groups free of aliphatic unsaturation are preferred.

Exemplary of the organohydrogenpolysiloxane are 1,1,3,3-tetramethyldisiloxane, 1,3,5,7-tetramethylcyclotetrasiloxane, methylhydrogencyclopolysiloxane, methylhydrogensiloxane-dimethylsiloxane cyclic copolymers, tris(dimethylhydrogensiloxy)methylsilane, tris(dimethylhydrogensiloxy)phenylsilane, methylhydrogenpolysiloxane capped with trimethylsiloxy at both ends of the molecular chain, dimethylsiloxane-methylhydrogensiloxane copolymers capped with trimethylsiloxy at both ends of the molecular chain, dimethylpolysiloxane capped with dimethylhydrogensiloxy at both ends of the molecular chain, dimethylsiloxane-methylhydrogensiloxane copolymers capped with dimethylhydrogensiloxy at both ends of the molecular chain, methylhydrogenpolysiloxane capped with dimethylhydrogensiloxy at both ends of the molecular chain, methylhydrogensiloxane-diphenylsiloxane copolymers capped with trimethylsiloxy at both ends of the molecular chain, methylhydrogensiloxane-diphenylsiloxane-dimethylsiloxane copolymers capped with trimethylsiloxy at both ends of the molecular chain, copolymers composed of $(CH_3)_2HSiO_{1/2}$ units and $SiO_{4/2}$ units, and copolymers composed of $(CH_3)_2HSiO_{1/2}$ units, $SiO_{4/2}$ units and $(C_6H_5)SiO_{3/2}$ units.

The molecular structure of the organohydrogenpolysiloxane may be straight, cyclic, branched or three-dimensional network. The number of silicon atoms per molecule or the degree of polymerization is typically 2 to about 1,000, preferably 3 to about 300, and especially 4 to about 100. Also preferably, the organopolysiloxane has a viscosity of 10 to 100,000 mPa-s, and more preferably 10 to 5,000 mPa-s at 23° C.

In the composition, the organopolysiloxane having silicon-bonded hydrogen atoms is preferably blended in such amounts as to provide 0.1 to 4.0 moles of silicon-bonded hydrogen atoms per mole of silicon-bonded alkenyl groups in components (A) and (B). If the amount of component (C) is below the lower limit of the range, the resulting composition may not fully cure. If the amount of component (C) is above the upper limit of the range, the cured product may become so hard that many cracks will form on the surface.

Component (D) is a hydrosilylation or addition reaction catalyst for promoting hydrosilylation addition reaction between alkenyl groups in components (A) and (B) and SiH groups in component (C). Suitable addition reaction catalysts are platinum group metal-based catalysts including platinum catalysts such as platinum black, platinic chloride, chloroplatinic acid, reaction products of chloroplatinic acid with monohydric alcohols, complexes of chloroplatinic acid with olefins, and platinum bisacetoacetate as well as palladium catalysts and rhodium catalysts. The amount of the addition reaction catalyst blended is a catalytic amount and usually about 0.1 to 1,000 ppm, specifically about 0.5 to 500 ppm, and more specifically about 1 to 200 ppm of platinum group metal based on the total weight of components (A), (B) and (C).

Blended as component (E) in the hydrophilic organopolysiloxane composition of the invention is one or multiple polyethers having the average compositional formula (2):

$$R^1O(C_2H_4O)_m(C_3H_6O)_nR^1 \quad (2)$$

wherein $R^1$ is a group $C_3H_6SiR^2_k(OR^2)_{3-k}$ or a monovalent hydrocarbon group, $R^2$ is a monovalent hydrocarbon group, k is 0, 1, 2 or 3, preferably 0 or 1, a plurality of $R^1$ and a plurality of $R^2$ may be the same or different, at least two of $R^1$ and $R^2$ are alkenyl, m is an integer of 0 to 100, n is an integer of 0 to 350, and m+n is an integer of 3 to 350, the polyether containing at least two alkenyl groups in a molecule.

In formula (2), the monovalent hydrocarbon groups represented by $R^1$ and $R^2$ are preferably of 1 to 12 carbon atoms, and more preferably 1 to 10 carbon atoms. Examples of the monovalent hydrocarbon groups represented by $R^1$ and R² include alkyl groups such as methyl, ethyl, propyl, butyl, pentyl, and hexyl; alkenyl groups of 2 to 6 carbon atoms, preferably 2 to 4 carbon atoms such as vinyl, allyl, butenyl, and isopropenyl; cycloalkyl groups such as cyclopentyl and cyclohexyl; aryl groups such as phenyl, tolyl, and xylyl; aralkyl groups such as benzyl and phenethyl; and haloalkyl groups such as 3,3,3-trifluoropropyl and 3-chloropropyl. Of these, alkyl and alkenyl groups are preferred. More preferably, $R^1$ is methyl, ethyl, vinyl, allyl or lauryl, and $R^2$ is methyl, ethyl, isopropenyl, vinyl or allyl. At least two of $R^1$ and $R^2$ are alkenyl. In this context, it is preferred for $R^2$ that $R^2$ directly attached to the silicon atom be alkenyl, and it is preferred for $R^1$ that two $R^1$ be both alkenyl. The subscript m is an integer of 0 to 100, n is an integer of 0 to 350, and m+n is an integer of 3 to 350, preferably m is 0 or an integer of 1 to 50, n is 0 or an integer of 1 to 320, and m+n is an integer of 3 to 320, more preferably m is 0 or an integer of 3 to 20, n is 0 or an integer of 5 to 200, and m+n is an integer of 3 to 200, and even more preferably m is 0 or an integer of 5 to 20, n is 0 or an integer of 5 to 100, and m+n is an integer of 5 to 100. In the molecule, $(C_2H_4O)$ and $(C_3H_6O)$ units may be arranged in blocks or randomly. If the degree of polymerization of the polyether (equal to m, n or m+n) is too low, it may be sometimes difficult to impart satisfactory hydrophilicity. If the degree of polymerization is too high, the composition or cured product thereof may allow the polyether to separate therefrom with the lapse of time or be less resistant to weathering.

It preferably has a number average molecular weight of the order of 150 to 20,000, and more preferably 200 to 15,000.

The amount of component (E) blended is preferably 10 to 100 parts, more preferably 10 to 50 parts, and even more preferably 20 to 50 parts by weight per 100 parts by weight of components (A), (B) and (C) combined. If the amount of component (E) blended is too small, it may become difficult for the polyether to impart satisfactory hydrophilicity to the composition. If amount of component (E) blended is too large, the composition or cured product thereof may allow the polyether to separate therefrom with the lapse of time, and sometimes the weathering resistance the organopolysiloxane structure inherently possesses may be compromised. Notably, in the composition of the invention, the alkenyl-containing polyether as component (E) may be optionally used in combination with an ordinary polyether component free of alkenyl groups in the molecule (e.g., endcapped with hydroxyl or similar groups).

While the hydrophilic organopolysiloxane composition for use as dental impression material according to the invention comprises components (A) to (E) as essential components, it may optionally comprise a nonfunctional diorganopolysiloxane containing at least 3 mol % of diphenylsiloxane units or at least 6 mol % of methylphenylsiloxane units, and free of silicon-bonded alkenyl groups as component (F). Note that the term "nonfunctional" means that the diorganopolysiloxane does not participate in hydrosilylation addition reaction. In an embodiment wherein a dimethylpolysiloxane containing alkenyl groups, but not phenyl groups in a molecule is used as component (A) or base polymer, for example, this nonfunctional, phenyl-containing diorganopolysiloxane as component (F), combined with the organopolysiloxane resinous copolymer as component (B), functions to inhibit the polyether component from separating out of the composition or cured product thereof with the lapse of time. The nonfunctional, phenyl-containing diorganopolysiloxane as component (F) contains at least 3 mol %, specifically 3 to 50 mol %, preferably 5 to 40 mol %, and more preferably 10 to 30 mol % of diphenylsiloxane units in the diorganosiloxane units of which the main chain is composed, or at least 6 mol %, specifically 6 to 50 mol %, preferably 10 to 40 mol %, and more preferably 20 to 35 mol % of methylphenylsiloxane units in the diorganosiloxane units of which the main chain is composed. If the content of diphenylsiloxane or methylphenylsiloxane units is below the range, the effect of inhibiting separation of the polyether component may not be fully exerted. Most often, the nonfunctional, phenyl-containing diorganopolysiloxane as component (F) has the average compositional formula (iii):

$$R^5{}_a SiO_{(4-a)/2} \qquad (iii)$$

wherein $R^5$ is each independently a substituted or unsubstituted monovalent hydrocarbon group of 1 to 10 carbon atoms, and preferably 1 to 8 carbon atoms, other than alkenyl, and "a" is a positive number of 1.5 to 2.8, preferably 1.8 to 2.5, and more preferably 1.95 to 2.05.

Examples of the silicon-bonded, substituted or unsubstituted, monovalent hydrocarbon groups (other than alkenyl) represented by $R^5$ include alkyl groups such as methyl, ethyl, propyl, isopropyl, butyl, isobutyl, tert-butyl, pentyl, neopentyl, hexyl, cyclohexyl, octyl, nonyl and decyl; aryl groups such as phenyl, tolyl, xylyl, and naphthyl; aralkyl groups such as benzyl, phenylethyl, and phenylpropyl; and substituted forms of the foregoing groups in which some or all hydrogen atoms are replaced by halogen atoms (e.g., fluoro, bromo, chloro), cyano groups or the like, for example, halo-substituted alkyl groups such as chloromethyl, chloropropyl, bromoethyl and trifluoropropyl, and cyanoethyl.

The organopolysiloxane preferably has a viscosity at 23° C. of 10 to 500,000 mPa-s, more preferably 400 to 200,000 mPa-s. A viscosity of less than 10 mPa-s at 23° C. invites a tendency that the resulting silicone rubber has substantially degraded physical properties. A viscosity in excess of 500,000 mPa-s invites a tendency that the resulting silicone rubber is inefficient to handle or work. The molecular structure of the organopolysiloxane is not particularly limited, and linear, branched, partially branched linear, and dendritic or three-dimensional network structures are suitable. Preferred is a linear diorganopolysiloxane having a main chain consisting essentially of repeating diorganosiloxane units and capped with triorganosiloxy groups at both ends of the molecular chain. Also, the organopolysiloxane may be a homopolymer having such a molecular structure, a copolymer having such a molecular structure, or a mixture of these polymers. The organopolysiloxane may contain at least 3 mol % of diphenylsiloxane units or at least 6 mol % of methylphenylsiloxane units in the diorganosiloxane units of the main chain, when taken as the overall component (F). Then, the desired effect is achievable with a mixture of 50% by weight of a dimethylpolysiloxane capped with trimethylsiloxy at both ends of the molecular chain and containing 12 mol % of methylphenylsiloxane and 50% by weight of a dimethylpolysiloxane capped with trimethylsiloxy at both ends of the molecular chain, for example.

Examples of the organopolysiloxane serving as component (F) include dimethylpolysiloxane capped with trimethylsiloxy at both ends of the molecular chain, dimethylpolysiloxane capped with hydroxydimethylsiloxy at both ends of the molecular chain, dimethylsiloxane (80 mol %)-methylphenylsiloxane (20 mol %) copolymers capped with trimethylsiloxy at both ends of the molecular chain, dimethylsiloxane (80 mol %)-diphenylsiloxane (20 mol %) copolymers capped with trimethylsiloxy at both ends of the molecular chain, dimethylsiloxane (97 mol %)-diphenylsiloxane (3 mol %) copolymers capped with trimethylsiloxy at both ends of the molecular chain, dimethylsiloxane (94 mol %)-methylphenylsiloxane (6 mol %) copolymers capped with trimethylsiloxy at both ends of the molecular chain, dimethylsiloxane (80 mol %)-methylphenylsiloxane (20 mol %) copolymers capped with hydroxydimethylsiloxy at both ends of the molecular chain, and dimethylsiloxane (80 mol %)-diphenylsiloxane (20 mol %) copolymers capped with hydroxydimethylsiloxy at both ends of the molecular chain.

The nonfunctional, phenyl-containing diorganopolysiloxane as component (F) may be blended in an amount of up to 50 parts (i.e., 0 to 50 parts), preferably up to 30 parts (i.e., 0 to 30 parts), and more preferably 1 to 20 parts by weight per 100 parts by weight of component (A).

While the hydrophilic organopolysiloxane composition comprises at least components (A) to (E) or if desired, components (A) to (F) as described above, it may further comprise other optional components as long as the objects of the invention are not impaired. Examples include reinforcing fillers such as fumed silica, wet microparticulate silica, crystalline silica, carbon black, red iron oxide, cerium oxide, titanium oxide, calcium carbonate, aluminum hydroxide, and titanates, and such fillers which have been surface treated with organosilicon compounds to be hydrophobic, addition reaction regulators such as acetylene compounds, hydrazine compounds, phosphine compounds, and mercaptan compounds, flame retardants, plasticizers, tackifiers, and the like.

The method of curing the inventive composition is not limited. Any standard methods may be employed, for example, a method of molding the composition and then allowing it to stand at room temperature, or a method of molding the composition and then heating at 50 to 200° C.

The state of the cured product thus obtained is not limited. For example, the cured product may range from a high hardness rubber to a low hardness rubber or gel. Cured products having a hardness of 5 to 90 on Durometer type A scale as prescribed in JIS K6253 are preferred because they are tightly adherent to members and easy to handle.

According to the invention, the inclusion of component (B) is effective for improving the tear strength of cured product and inhibiting the polyether component from separating out of the composition or cured product thereof with the lapse of time. Particularly when the composition is used as a dental impression material, accurate impressions can be taken. The cured product obtained according to the invention preferably has a tear strength of 5 to 50 kN/m as measured according to JIS K6252 using an unnotched angle shape.

The cured product resulting from the composition of the invention has a contact angle of up to 70°, more preferably up to 65°, and even more preferably up to 60°, as measured according to JIS R3257. Although the lower limit of contact angle need not be specified, it is usually at least 20°, and preferably at least 30°.

EXAMPLE

Examples and Comparative Examples are given below for further illustrating the invention although the invention is not limited thereto. The viscosity is a measurement at 23° C.

Examples and Comparative Examples

Organopolysiloxane compositions were prepared according to the formulation shown in Tables. They were cured under the conditions shown in Tables, and the cured products measured for hardness by type A durometer according to JIS K6253 and for tear strength according to JIS K6252 using an unnotched angle shape. They were also measured for contact angle according to JIS R3257.

The base polymers, base resin, and polyethers used herein are identified below.

Base Polymer 1
   α, ω-vinyldimethylsiloxy-capped dimethylsiloxane-diphenylsiloxane copolymer (viscosity=4,000 mPa-s, a content of diphenylsiloxane units in diorganosiloxane unit main chain=30 mol %)

Base Polymer 2
   α, ω-vinyldimethylsiloxy-capped dimethylsiloxane-diphenylsiloxane copolymer (viscosity=3,000 mPa-s, a content of diphenylsiloxane units in diorganosiloxane unit main chain=10 mol %)

Base Polymer 3
   α, ω-vinyldimethylsiloxy-capped dimethylpolysiloxane (viscosity=4,000 mPa-s)

Base Polymer 4
   α, ω)-trimethylsiloxy-capped dimethylsiloxane-diphenylsiloxane copolymer (viscosity=100 mPa-s, a content of diphenylsiloxane units in diorganosiloxane unit main chain=10 mol %)

Base Resin 1
   polysiloxane consisting of $Me_3SiO_{0.5}$, $Me_2ViSiO_{0.5}$ and $SiO_2$ units in $(Me_3SiO_{0.5}+Me_2ViSiO_{0.5})/SiO_2$ ratio of 0.8 (an alkenyl content=0.08 mol % based on entire silicon-bonded organic groups, solid at 23° C., Me: methyl, Vi: vinyl)

Polyether 1

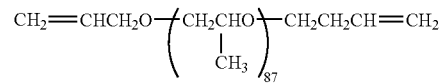

Polyether 2

Polyether 3

Naroacty N-40 (polyoxyethylene alkyl ether, Sanyo Chemicals Industries, Ltd.)

TABLE 1

|  | Example |  |  |
|---|---|---|---|
| Amount (pbw) | 1 | 2 | 3 |
| Base polymer 1 | 70 | 80 | 80 |
| Base polymer 2 | 20 | | |
| Base resin 1 | 10 | 20 | 20 |
| R-972 (Nippon Aerosil Co., Ltd.) | | 10 | 10 |
| Polyether 1 | 30 | 30 | 40 |
| Polyether 2 | 10 | 10 | 10 |
| Polyether 3 | 10 | 10 | |
| Pt catalyst[1] | 1.5 | 1.5 | 1.5 |
| Regulator[2] | 0.01 | 0.01 | 0.01 |
| Curing agent[3] | 18 | 20 | 21 |
| Curing conditions: 23° C., 1 hour | | | |
| Hardness, Type A | 45 | 50 | 45 |
| Tear strength (angle), kN/m | 7 | 15 | 15 |
| Contact angle, ° | 30 | 30 | 40 |

TABLE 2

|  | Example |  |  |  |
|---|---|---|---|---|
| Amount (pbw) | 4 | 5 | 6 | 7 |
| Base polymer 3 | 90 | 80 | 80 | 80 |
| Base polymer 4 | | | | 10 |
| Base resin 1 | 10 | 20 | 20 | 10 |
| R-972 (Nippon Aerosil Co., Ltd.) | | 10 | 10 | 10 |
| Polyether 1 | 30 | 30 | 40 | 30 |
| Polyether 2 | 10 | 10 | 10 | 10 |
| Polyether 3 | 10 | 10 | | 10 |
| Pt catalyst[1] | 1.5 | 1.5 | 1.5 | 1.5 |
| Regulator[2] | 0.01 | 0.01 | 0.01 | 0.01 |
| Curing agent[3] | 18 | 20 | 21 | 15 |
| Curing conditions: 23° C., 1 hour | | | | |
| Hardness, Type A | 45 | 55 | 50 | 45 |
| Tear strength (angle), kN/m | 7 | 17 | 16 | 40 |
| Contact angle, ° | 30 | 30 | 40 | 30 |

TABLE 3

|  | Comparative Example |  |  |  |  |
|---|---|---|---|---|---|
| Amount (pbw) | 1 | 2 | 3 | 4 | 5 |
| Base polymer 1 | 70 | 100 | 100 | 70 | 100 |
| Base polymer 2 | 30 | | | 20 | |
| Base resin 1 | | | | 10 | 10 |
| R-972 (Nippon Aerosil Co., Ltd.) | | 10 | 10 | | |
| Polyether 1 | 30 | 30 | 40 | | |
| Polyether 2 | 10 | 10 | 10 | | |
| Polyether 3 | 10 | 10 | | 40 | 40 |
| Pt catalyst[1] | 1.5 | 1.5 | 1.5 | 1.5 | 1.5 |
| Regulator[2] | 0.01 | 0.01 | 0.01 | 0.01 | 0.01 |
| Curing agent[3] | 16 | 17 | 18 | 9 | 9 |
| Curing conditions: 23° C., 1 hour | | | | | |
| Hardness, Type A | 40 | 40 | 35 | 25 | 20 |
| Tear strength (angle), kN/m | 3 | 5 | 5 | 2 | 1 |
| Contact angle, ° | 30 | 30 | 40 | 30 | 30 |

[1] toluene solution of platinum 1,3-divinyl-1,1,3,3-tetramethyl-disiloxane complex having a platinum content of 0.5 wt %
[2] 50% toluene solution of 1-ethynyl cyclohexanol
[3] dimethylsiloxane-methylhydrogensiloxane copolymer capped with dimethylsiloxy at both ends of the molecular chain having a viscosity of 10 mPa·s (silicon-bonded hydrogen atom content = 33 wt %)

The invention claimed is:

1. A hydrophilic organopolysiloxane composition of the hydrosilylation reaction cure type for use as dental impression material, comprising as essential components,
   (A) a diorganopolysiloxane having at least 0.1 silicon-bonded alkenyl group in a molecule,
   (B) a liquid or solid organopolysiloxane having the average compositional formula (1):

$$R_p SiO_{(4-p)/2} \tag{1}$$

wherein R is each independently a substituted or unsubstituted monovalent hydrocarbon group, alkoxy or hydroxyl group, 0.1 to 80 mol % of the entire R being alkenyl, and p is a positive number satisfying $1 \leq p < 2$, said organopolysiloxane comprising $SiO_2$ units and $R_3SiO_{1/2}$ units and having a viscosity of at least 10 mPa·s at 23° C.,
   (C) an organohydrogenpolysiloxane having at least two silicon-bonded hydrogen atoms in a molecule,
   (D) a hydrosilylation catalyst, and
   (E) a polyether having the average compositional formula (2):

$$R^1 O(C_2H_4O)_m(C_3H_6O)_n R^1 \tag{2}$$

wherein $R^1$ is a group $C_3H_6SiR^2{}_k(OR^2)_{3-k}$ or a monovalent hydrocarbon group, $R^2$ is a monovalent hydrocarbon group, k is 0, 1, 2 or 3, a plurality of $R^1$ and a plurality of $R^2$ may be the same or different, at least two of $R^1$ and $R^2$ are alkenyl, m is an integer of 0 to 100, n is an integer of 0 to 350, and m+n is an integer of 3 to 350,
   said component (E) being present in an amount of 10 to 100 parts by weight per 100 parts by weight of components (A), (B), and (C) combined.

2. The hydrophilic organopolysiloxane composition for use as dental impression material of claim 1, further comprising as an essential component (F) a diorganopolysiloxane containing at least 3 mol % of diphenylsiloxane units or at least 6 mol % of methylphenylsiloxane units, and free of silicon-bonded alkenyl groups in a molecule.

3. The hydrophilic organopolysiloxane composition for use as dental impression material of claim 1, wherein component (E) is present in an amount of 10 to 50 parts by weight per 100 parts by weight of components (A), (B), and (C) combined.

4. The hydrophilic organopolysiloxane composition for use as dental impression material of claim 1, wherein the organopolysiloxane as component (B) is a resinous copolymer comprising $SiO_2$ units, $R_3SiO_{1/2}$ units, $R_2SiO_{2/2}$ units and $RSiO_{3/2}$ units wherein R is as defined above, the molar ratio of $R_3SiO_{1/2}$ units to $SiO_2$ units being from 0.5:1 to 1.5:1, and $R_2SiO_{2/2}$ units and $RSiO_{3/2}$ units being contained in a total amount of 0 to 50% based on the total weight of the organopolysiloxane resinous copolymer.

5. The hydrophilic organopolysiloxane composition for use as dental impression material of claim 1, wherein the amount of organopolysiloxane (B) blended is 5 to 50 parts by weight per 100 parts by weight of component (A).

6. The hydrophilic organopolysiloxane composition for use as dental impression material of claim 1, wherein the organohydrogenpolysiloxane as component (C) is blended in such an amount as to provide 0.1 to 4.0 moles of silicon-bonded hydrogen atoms per mol of silicon-bonded alkenyl groups in components (A) and (B).

7. The hydrophilic organopolysiloxane composition for use as dental impression material of claim 2, wherein the diorganopolysiloxane as component (F) is blended in an amount of 1 to 50 parts by weight per 100 parts by weight of component (A).

8. The hydrophilic organopolysiloxane composition for use as dental impression material of claim 2, wherein component (E) is present in an amount of 10 to 50 parts by weight per 100 parts by weight of components (A), (B), and (C) combined.

9. The hydrophilic organopolysiloxane composition for use as dental impression material of claim 2, wherein the organopolysiloxane as component (B) is a resinous copolymer comprising $SiO_2$ units, $R_3SiO_{1/2}$ units, $R_2SiO_{2/2}$ units and $RSiO_{3/2}$ units wherein R is as defined above, the molar ratio of $R_3SiO_{1/2}$ units to $SiO_2$ units being from 0.5:1 to 1.5:1, and $R_2SiO_{2/2}$ units and $RSiO_{3/2}$ units being contained in a total amount of 0 to 50% based on the total weight of the organopolysiloxane resinous copolymer.

10. The hydrophilic organopolysiloxane composition for use as dental impression material of claim 2, wherein the amount of organopolysiloxane (B) blended is 5 to 50 parts by weight per 100 parts by weight of component (A).

11. The hydrophilic organopolysiloxane composition for use as dental impression material of claim 2, wherein the organohydrogenpolysiloxane as component (C) is blended in such an amount as to provide 0.1 to 4.0 moles of silicon-bonded hydrogen atoms per mol of silicon-bonded alkenyl groups in components (A) and (B).

* * * * *